US006696255B2

(12) United States Patent
Dattagupta

(10) Patent No.: US 6,696,255 B2
(45) Date of Patent: *Feb. 24, 2004

(54) NUCLEIC ACID HAIRPIN PROBES AND USES THEREOF

(75) Inventor: Nanibhushan Dattagupta, San Diego, CA (US)

(73) Assignee: Applied Gene Technologies, Inc., San Diego, CA (US)

( * ) Notice: Subject to any disclaimer, the term of this patent is extended or adjusted under 35 U.S.C. 154(b) by 82 days.

This patent is subject to a terminal disclaimer.

(21) Appl. No.: 09/995,686

(22) Filed: Nov. 29, 2001

(65) Prior Publication Data

US 2002/0110826 A1 Aug. 15, 2002

Related U.S. Application Data

(62) Division of application No. 09/616,761, filed on Jul. 14, 2000, now Pat. No. 6,380,377.

(51) Int. Cl.[7] .......................... C12Q 1/68; C12P 19/34; G01N 33/00; C07H 21/02; C07H 21/04
(52) U.S. Cl. .......................... 435/6; 435/91.1; 436/94; 536/23.1; 536/24.3
(58) Field of Search .................. 435/6, 91.1, 91.2, 435/183; 436/94; 536/23.1, 24.3, 24.33, 25.3, 25.32

(56) References Cited

U.S. PATENT DOCUMENTS

| 4,134,792 A | 1/1979 | Boguslaski et al. | 195/99 |
|---|---|---|---|
| 4,230,797 A | 10/1980 | Boguslaski et al. | 435/7 |
| 4,238,565 A | 12/1980 | Hornby et al. | 435/7 |

(List continued on next page.)

FOREIGN PATENT DOCUMENTS

GB 1548741 7/1979
WO WO 98/10183 6/1992

OTHER PUBLICATIONS

Beaucage and Carruthers. (1981). *Tetrahedron Lett* 22:1859–1862.
Beenhouwer et al. (1995). *Tubercule and Lung Disease* 76:425–430.
Block and Kramer. (1977). *Molecular and Cellular probes* 11:187–194.
Dattagupta et al. (1989). *Anal Biochem* 117:85–89.
Forster et al. (1985). *Nucleic Acid Res* 13:745–761.
Fujiwara and Oishi. (1998). *Nucleic Acids Res* 26:5728–5733.
Gorus and Schram. (1979). *Clin Chem* 25:512–519.
Hertzberg et al. (1982). *J Am Chem Soc* 104:313–315.
Kanehisa. (1984). *Nucleic Acid Res* 12:203–213.
Matteucci et al. (1981). *J Am Chem Soc* 103:3185–3191.
Mergny et al. (1994). *Nucleic Acids Res* 22:920–928.
Mitchell et al. (1982). *J Am Chem Soc* 104:4265–4266.
Saiki et al. (1989). *Proc Natl Acad Sci USA* 86:6230–6234.
Soini and Hemmila. (1979). *Clin Chem* 25:353–361.
Sriprakash and Hartas. (1989). *Gene Anal Techn* 6:29–32.
Telenti et al. (1993). *Lancet* 341:647–650.
Tyagi and Kramer. (1996). *Nature Biotech* 14:303–309.
White et al. (1977). *Meth Enzymol* 46:644–649.
Wisdom. (1976). *Clin Chem* 22:1243–1255.
Yershov et al. (1996) *Proc. Natl. Acad. Sci. USA* 93:4913–4918.

*Primary Examiner*—Ethan Whisenant
*Assistant Examiner*—Frank Lu
(74) *Attorney, Agent, or Firm*—Pennie & Edmonds LLP

(57) ABSTRACT

This invention relates generally to nucleic acid hybridization analysis. More specifically, oligonucleotide probes containing hairpin structures, or arrays of such oligonucleotide probes immobilized on a solid support, that are suitable for hybridization analysis are provided. Methods for nucleic acid hybridization analysis using the probes or array of immobilized probes are also provided.

24 Claims, 1 Drawing Sheet

U.S. PATENT DOCUMENTS

| | | |
|---|---|---|
| 5,119,801 A | 6/1992 | Eizenhoefer et al. ... 128/24 EL |
| 5,143,854 A | 9/1992 | Pirrung et al. .............. 436/518 |
| 5,149,797 A | 9/1992 | Pederson et al. ............. 536/27 |
| 5,288,514 A | 2/1994 | Ellman .......................... 427/2 |
| 5,312,233 A | 5/1994 | Tanny et al. ................. 417/316 |
| 5,312,728 A | 5/1994 | Lizardi et al. .................. 435/6 |
| 5,348,855 A | 9/1994 | Dattagupta et al. ............ 435/6 |
| 5,384,261 A | 1/1995 | Winkler et al. ............. 436/518 |
| 5,541,061 A | 7/1996 | Fodor et al. .................... 435/6 |
| 5,541,313 A | 7/1996 | Ruth ........................ 536/24.3 |
| 5,556,752 A | 9/1996 | Lockhart et al. ............... 435/6 |
| 5,561,071 A | 10/1996 | Hollenberg et al. ............ 437/1 |
| 5,587,472 A | 12/1996 | Dattagupta et al. ......... 536/26.2 |
| 5,607,834 A | 3/1997 | Bagwell ........................ 435/6 |
| 5,616,731 A | 4/1997 | Lobberding et al. ........ 549/282 |
| 5,677,195 A | 10/1997 | Winkler et al. ............. 436/518 |
| 5,741,644 A | 4/1998 | Kambara et al. ............... 435/6 |
| 5,861,242 A | 1/1999 | Chee et al. .................... 435/5 |
| 5,866,336 A | 2/1999 | Nazarenko et al. ............ 435/6 |
| 5,932,450 A | 8/1999 | Dattagupta et al. ........ 435/91.1 |
| 5,945,312 A | 8/1999 | Goodman et al. .......... 435/91.1 |
| 6,024,138 A | 2/2000 | Fritz et al. .................... 141/31 |
| 6,114,121 A | 9/2000 | Fujiwara et al. ............... 435/6 |
| 6,277,607 B1 | 8/2001 | Tyagi et al. ................ 435/91.2 |

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Hairpin probe

<400> SEQUENCE: 1
catccgtaac tacatcttcc a                                              21

<210> SEQ ID NO 2
<211> LENGTH: 51
<212> TYPE: DNA
<213> ORGANISM: Artificial Sequence
<220> FEATURE:
<223> OTHER INFORMATION: Hairpin probe

<400> SEQUENCE: 2
catccgtaac tacatcttcc atttttttttt tggaagatgt agttacggat g            51

<210> SEQ ID NO 3
<211> LENGTH: 25
<212> TYPE: DNA
<213> ORGANISM: Artificial Sequence
<220> FEATURE:
<223> OTHER INFORMATION: PCR primer

<400> SEQUENCE: 3
gagaattcgg tcggcgagct gatcc                                          25

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4
cgaagcttga cccgcgcgta cacc                                           24

<210> SEQ ID NO 5
<211> LENGTH: 57
<212> TYPE: DNA
<213> ORGANISM: Artificial Sequence
<220> FEATURE:
<223> OTHER INFORMATION: Hairpin probe

<400> SEQUENCE: 5
caattcatgg accagaacaa cccgtttttt tttcgggttg ttctgctcca tgaattg       57

<210> SEQ ID NO 6
<211> LENGTH: 18
<212> TYPE: DNA
<213> ORGANISM: Artificial Sequence
<220> FEATURE:
<223> OTHER INFORMATION: Hairpin probe

<400> SEQUENCE: 6
tttttttttc aattcatg                                                  18

<210> SEQ ID NO 7
<211> LENGTH: 48

-continued

```
<212> TYPE: DNA
<213> ORGANISM: Artificial Sequence
<220> FEATURE:
<223> OTHER INFORMATION: Hairpin probe

<400> SEQUENCE: 7
gaccagaaca acccgttttt ttttcgggtt gttctgctcc atgaattg        48
```

NUCLEIC ACID HAIRPIN PROBES AND USES THEREOF

This application is a divisional of U.S. Ser. No. 09/616,761 filed Jul. 14, 2000, now U.S. Pat. No. 6,380,377, the content of which is incorporated herein by reference in its entirety.

FIELD OF THE INVENTION

This invention relates generally to nucleic acid hybridization analysis. More specifically, an oligonucleotide probe for hybridization analysis is provided, that comprises a nucleotide sequence which, under suitable conditions, is capable of forming a hairpin structure. The double stranded segment of the hairpin structure is formed between two perfectly matched nucleotide sequences, and at least a portion of the nucleotide sequence within the double stranded segment is complementary to a target nucleotide sequence to be detected. An array of oligonucleotide probes immobilized on a solid support for hybridization analysis is also provided that comprises a solid support suitable for use in nucleic acid hybridization having immobilized thereon a plurality of oligonucleotide probes. The probes each comprise a nucleotide sequence which, under suitable conditions, is capable of forming a hairpin structure having a nucleotide sequence complementary to a target nucleotide sequence to be detected located within the double stranded segment. Methods for nucleic acid hybridization analysis using the probes or array of immobilized probes are additionally provided.

BACKGROUND OF THE INVENTION

Nucleic acid hybridization, in the forty years since its discovery, has become a powerful tool with implications for biology, medicine and industry. Hybridization assays are based on the very specific base pairing that is found in hybrids of DNA and RNA. Base sequences of analytical interest appearing along a strand of nucleic acid can be detected very specifically and sensitively by observing the formation of hybrids in the presence of a probe nucleic acid known to comprise a base sequence that is complementary with the sequence of interest. Nucleic acid hybridization has been used for a wide variety of purposes including, for example, identification of specific clones from cDNA and genomic libraries, detecting single base pair polymorphisms in DNA, generating mutations by oligonucleotide mutagenesis, amplifying nucleic acids from single cells or viruses, or detecting microbial infections.

Recent advances in nucleic acid hybridization methods have greatly expanded the scope and extent of its potential applications. Of great interest are approaches to miniaturize hybridization reactions by preparing "microarray biochips" (or "DNA chips") containing large numbers of oligonucleotide probes prepared, for example, through VLSIPST™ technology (See U.S. Pat. Nos. 5,143,854 or 5,561,071). These approaches offer great promise for a wide variety of applications. Microarray biochips are useful for sequencing nucleic acid by hybridization (see, for example, U.S. Pat. No. 5,741,644), for diagnosis of human immunodeficiency virus (see, for example, U.S. Pat. No. 5,861,242) and for screening potential DNA binding drugs (see, for example, U.S. Pat. No. 5,556,752).

When using nucleic acid microarrays, there are two general approaches for detecting hybridization to a nucleic acid. Detection can be accomplished if the target nucleic acid is labeled ("direct labeling approach"). Alternatively, detection can be accomplished by a second probe that is detectably labeled and which can hybridize to the nucleic acid of the sample, which is hybridized to the first probe immobilized on the array ("indirect" labeling approach).

Bagwell, U.S. Pat. No. 5,607,834 discloses a fluorescent probe for binding to a polynucleotide target and methods using such fluorescent probes that comprises: an oligonucleotide having a segment complementary to the polynucleotide target, the oligonucleotide forming two imperfect hairpins both of which together include the segment except for one nucleotide; and one donor fluorophore and one acceptor fluorophore covalently attached to the oligonucleotide so that only when the imperfect hairpins are formed, the donor fluorophore and the acceptor fluorophore are in close proximity to allow resonance energy transfer therebetween. The fluorescent probes disclosed in Bagwell must contain "imperfect hairpins," i.e., containing mismatches in the double-stranded stem segment. In addition, Bagwell does not disclose or teach any immobilized arrays of oligonucleotide probes.

Nazarenko et al., U.S. Pat. No. 5,866,336 disclose an oligonucleotide containing a hairpin structure for use as a primer in detecting a target nucleotide sequence. Similar probes are described in Mergny et al., *Nucleic Acids Res.*, 22:920–928 (1994). Blok and Kramer, *Molecular and Cellular Probes*, 11:187–194 (1997) describe an amplification RNA probe containing a molecular switch, i.e., a plurality of hairpin structures. Fujiwara and Oishi, *Nucleic Acids Res.*, 26:5728–5733 (1998) describe a method of covalent attachment of probe DNA to double-stranded target DNA where an imperfect hairpin was used to hybridize to a target DNA. Sriprakash and Hartas, *Gene Anal. Techn.*, 6:29–32 (1989) describe a method of generating radioisotope labeled probe with hairpin nucleic acid structure. One common feature of the hairpin structure-containing probes described in the above references is that the nucleotide sequence complementary to a target nucleotide sequence always resides in the single-stranded, not double-stranded, segment of the hairpin structure.

The direct labeling approach can be problematic because nucleic acid labeling methods may fail to label different nucleic acids in a mixture equally. In addition, direct labeling may introduce mutations or other chemical modifications of the sample nucleic acid that prohibit or reduce hybridization.

Detection of hybridization in a microarray biochip by indirect labeling also can be problematic because background hybridization between the second probe may hybridize to the first probe immobilized on the microarray, giving rise to a high false-positive assay background. If the microarray utilizes only a single probe or very limited set of probes, the background may be reduced in the indirect labeling format by designing the specific second probe such that it does not hybridize to the immobilized probes on the array. However, when the microarray contains a wide variety of probe sequences for simultaneously detecting a variety of different nucleic acid targets (the reason for miniaturizing hybridization), designing second probes that are specific and that can avoid background hybridization to the immobilized probes becomes extremely difficult, if not impossible. Accordingly, a need exists for improved hybridization in general and for detecting hybridization on microarray formats in particular. The present invention addresses this and other related needs in the art.

SUMMARY OF THE INVENTION

In one aspect, the present invention provides an oligonucleotide probe for hybridization analysis, which probe comprises a nucleotide sequence which, under suitable conditions, is capable of forming a hairpin structure, wherein the double stranded segment of the hairpin structure is formed between two perfectly matched nucleotide sequences, and wherein at least a portion of the nucleotide sequence located within the double stranded segment is complementary to a target nucleotide sequence to be detected.

In another aspect, the present invention provides an array of oligonucleotide probes immobilized on a solid support for hybridization analysis, which array comprises a solid support suitable for use in nucleic acid hybridization having immobilized thereon a plurality of oligonucleotide probes, each of the probes comprising a nucleotide sequence which, under suitable conditions, is capable of forming a hairpin structure, wherein at least a portion of the nucleotide sequence located within the double stranded segment is complementary to a target nucleotide sequence to be detected.

In still another aspect, the present invention provides a method for detecting a target nucleotide sequence in a sample comprising the steps of: a) providing an oligonucleotide probe comprising a nucleotide sequence having a hairpin structure, with a double stranded segment, wherein the double stranded segment is formed between two complementary, preferably perfectly matched nucleotide sequences, and wherein at least a portion of the nucleotide sequence located within the double stranded segment is complementary to a target nucleotide sequence to be detected; b) contacting the probe provided in step a) with a sample containing or suspected of containing the target nucleotide sequence under conditions that favor intermolecular hybridization between the probe and the target nucleotide sequence over intramolecular hybridization of the probe itself; and c) assessing the intermolecular hybrid formed in step b), whereby presence of the intermolecular hybrid indicates the presence of the target nucleotide sequence in the sample.

In yet another aspect, the present invention provides a method for detecting a target nucleotide sequence in a sample comprising the steps of: a) providing an array of oligonucleotide probes immobilized on a solid support suitable for use in nucleic acid hybridization having immobilized thereon a plurality of oligonucleotide probes, each of the probes comprising a hairpin structure with a double stranded segment and wherein at least a portion of the nucleotide sequence located within the double stranded segment is complementary to a target nucleotide sequence to be detected; b) contacting the array of probes provided in step a) with a sample containing or suspected of containing the target nucleotide sequence under conditions that favor intermolecular hybridization between the probes and the target nucleotide sequence over intramolecular hybridization of the probes themselves; and c) assessing the intermolecular hybrids formed in step b), whereby presence of the intermolecular hybrids indicates the presence of the target nucleotide sequence in the sample.

DETAILED DESCRIPTION OF THE INVENTION

Figure 1:
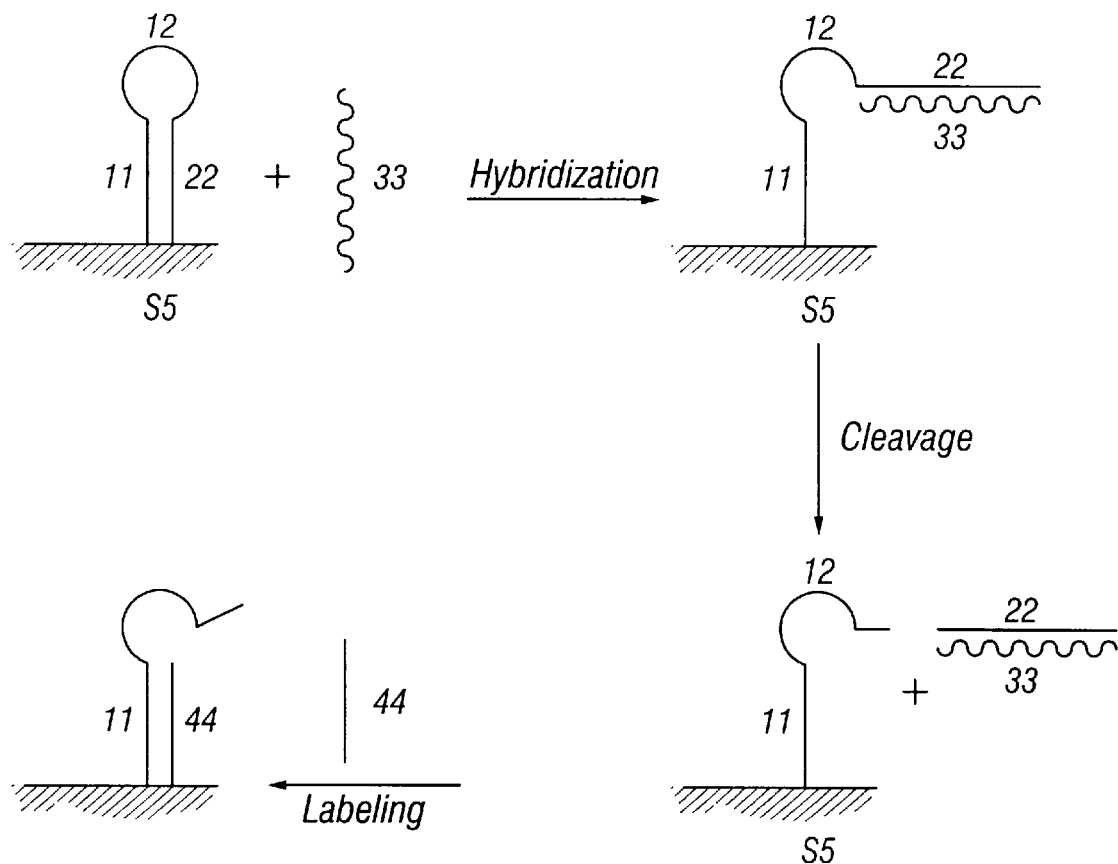
FIG. 1 illustrates one embodiment of nucleic acid hybridization analysis using an immobilized hairpin probe. SS depicts a solid support upon which the hairpin probe is immobilized. 11, 12, 22 are parts of an immobilized hairpin probe, wherein 11 and 22 forms the double-stranded stem region, 12 is the single-stranded loop region, which can be a non-nucleic acid moiety, and at least a portion of 22 is complementary to the target nucleotide sequence 33. Under suitable conditions, 22 forms a duplex with the target nucleotide sequence 33 and leaves 11 as a single-stranded region. The duplex formed between 22 and 33 is then cleaved off the immobilized probe, preferably with an enzyme, e.g., a RNase H or a restriction enzyme that recognizes a restriction enzyme cleavage site within the duplex. A labeled detecting probe, 44, is hybridized with the single-stranded region 11, which gives a readout signal for detecting hybridization between the hairpin probe and the target nucleotide sequence. If, in the original hybridization step, 22 and 33 are not complementary to each other and do not form a duplex, 11 is still masked by 22 and cannot be hybridized with the detecting probe 44, so no signal is detected.
Figure 2:
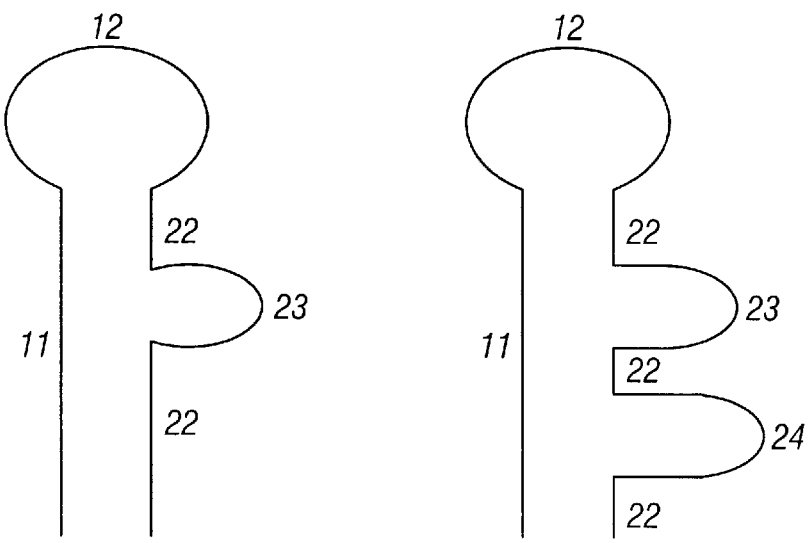
FIG. 2 illustrates hairpin probes with multiple single-stranded loop regions. 22, 23 and 24 are complementary to target nucleotide sequence. 12, 23 and 24 can be non-nucleic acid moieties, e.g., linked polyethylene glycols.

The present invention provides probes and methods for nucleic acid hybridization analysis with improved specificity. Central to this goal is the use of probes with a hairpin structure, preferably immobilized to a solid support, that are capable of intramolecular and intermolecular hybridization.

Intramolecular hybridization of the hairpin probe is accomplished by two complementary sequences in the probe running in opposite directions to each other, such that the bases in each sequence hybridize intramolecularly under the appropriate conditions, forming a double stranded loop within the probe, i.e., a hairpin structure. Intermolecular-hybridization of the hairpin probe is accomplished by designing the probes to contain a sequence complementary to the target nucleotide sequence.

A useful feature of the hairpin probes used herein is the overlap between the probe sequences involved in intramolecular hybridization with the probe. sequence involved in hybridizing intermolecularly with a target nucleic acid. By overlapping these sequences, a portion of the hairpin probe has the dual property of being able to engage in intramolecular or intermolecular hybridization. It is through such overlap that background hybridization from the direct or indirect detection method can be reduced thus improving specificity.

The greatest reduction in background hybridization results when the intramolecular hybridizing sequence of the hairpin probe overlaps completely with the intermolecular hybridizing sequence, although these two sequences need not be coextensive. Thus, when the hairpin probe has formed a hairpin structure through intramolecular hybridization, the intermolecular hybridization sequence is fully contained within a double stranded nucleic acid, making it unable to hybridize to a complementary detectably labeled probe sequence. Alternatively, one can design the hairpin probe such that only a portion of the intermolecular hybridization sequence overlaps with the intramolecular hybridization probe sequence.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications and sequences from GenBank and other data bases referred to herein are incorporated by reference in their entirety.

As used herein, "hairpin structure" refers to a polynucleotide or nucleic acid that contains a double-stranded stem segment and a single-stranded loop segment wherein the two polynucleotide or nucleic acid strands that form the double-stranded stem segment is linked and separated by the single polynucleotide or nucleic acid strand that forms the loop segment. The "hairpin structure" can also further comprise 3' and/or 5' single-stranded region(s) extending from the double-stranded stem segment.

As used herein, "two perfectly matched nucleotide sequences" refers to a nucleic acid duplex wherein the two nucleotide strands match according to the Watson-Crick basepair principle, i.e., A-T and C-G pairs in DNA:DNA duplex and A-U and C-G pairs in DNA:RNA or RNA:RNA duplex, and there is no deletion or addition in each of the two strands.

As used herein, "at least a portion of nucleotide sequence complementary to a target nucleotide sequence to be detected is located within said double stranded segment" refers to the fact at least 50% of the nucleotide sequence complementary to the target nucleotide sequence to be detected is located within said double stranded segment. Preferably, at least 60%, 70,%, 80%, 90%, 95%, 96%, 97%, 98%, 99% or 100% of the nucleotide sequence complementary to the target nucleotide sequence to be detected is located within said double stranded segment.

As used herein, "the nucleotide sequence complementary to a target nucleotide sequence to be detected is completely located within said double stranded segment" refers to the fact 100% of the nucleotide sequence complementary to the target nucleotide sequence to be detected is located within said double stranded segment.

As used herein, "conditions that favor intermolecular hybridization between said probe and said target nucleotide sequence over intramolecular hybridization of said probe itself" refers to the conditions under which the intermolecular hybrid can stably exist and be detected while the intramolecular hybrid cannot stably exist and be detected.

As used herein, "melting temperature" ("Tm") refers to the midpoint of the temperature range over which nucleic acid duplex, i.e., DNA:DNA, DNA:RNA and RNA:RNA, is denatured.

As used herein: "stringency of hybridization" in determining percentage mismatch is as follows:
1) high stringency: 0.1×SSPE, 0.1% SDS, 65° C.;
2) medium stringency: 0.2×SSPE, 0.1% SDS, 50° C. (also referred to as moderate stringency); and
3) low stringency: 1.0×SSPE, 0.1% SDS, 50° C.

It is understood that equivalent stringencies may be achieved using alternative buffers, salts and temperatures.

As used herein, "assessing" refers to quantitative and/or qualitative determination of the intermolecular hybrid formed between the hairpin probe and the target nucleotide sequence, e.g., obtaining an absolute value for the amount or concentration of the intermolecular hybrid, and also of obtaining an index, ratio, percentage, visual or other value indicative of the level of the intermolecular hybrid. Assessment may be direct or indirect and the chemical species actually detected need not of course be the intermolecular hybrid itself but may, for example, be a derivative thereof or some further substance.

As used herein, a "significant reduction in background hybridization" means that in the absence of a target containing nucleic acid sample, hybridization of the detectably labeled probe with the hairpin probe itself is reduced by at least 80%, more preferably by at least 90%, even more preferably by at least 95%, still more preferably by at least 99%.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein, "disease or disorder" refers to a pathological condition in an organism resulting from, e.g., infection or genetic defect, and characterized by identifiable symptoms.

As used herein, "neoplasm (neoplasia)" refers to abnormal new growth, and thus means the same as tumor, which may be benign or malignant. Unlike hyperplasia, neoplastic proliferation persists even in the absence of the original stimulus.

As used herein, "cancer" refers to a general term for diseases caused by any type of malignant tumor.

As used herein, "an immune system disease or disorder" refers to a pathological condition caused by a defect in the immune system. The immune system is a complex and highly developed system, yet its mission is simple: to seek and kill invaders. If a person is born with a severely defective immune system, death from infection by a virus, bacterium, fungus or parasite will occur. In severe combined immunodeficiency, lack of an enzyme means that toxic waste builds up inside immune system cells, killing them and thus devastating the immune system. A lack of immune system cells is also the basis for DiGeorge syndrome: improper development of the thymus gland means that T cell production is diminished. Most other immune disorders result from either an excessive immune response or an 'autoimmune attack'. For example, asthma, familial Mediterranean fever and Crohn disease (inflammatory bowel disease) all result from an over-reaction of the immune system, while autoimmune polyglandular syndrome and some facets of diabetes are due to the immune system attacking 'self' cells and molecules. A key part of the immune system's role is to differentiate between invaders and the body's own cells—when it fails to make this distinction, a reaction against 'self' cells and molecules causes autoimmune disease.

As used herein, "a metabolism disease or disorder" refers to a pathological condition caused by errors in metabolic processes. Metabolism is the means by which the body derives energy and synthesizes the other molecules it needs from the fats, carbohydrates and proteins we eat as food, by enzymatic reactions helped by minerals and vitamins. There is a significant level of tolerance of errors in the system: often, a mutation in one enzyme does not mean that the individual will suffer from a disease. A number of different enzymes may compete to modify the same molecule, and there may be more than one way to achieve the same end result for a variety of metabolic intermediates. Disease will only occur if a critical enzyme is disabled, or if a control mechanism for a metabolic pathway is affected.

As used herein, "a muscle and bone disease or disorder" refers to a pathological condition caused by defects in genes important for the formation and function of muscles, and connective tissues. Connective tissue is used herein as a broad term that includes bones, cartilage and tendons. For example, defects in fibrillin—a connective tissue protein that is important in making the tissue strong yet flexible—cause Marfan syndrome, while diastrophic dysplasia is caused by a defect in a sulfate transporter found in cartilage. Two diseases that originate through a defect in the muscle cells themselves are Duchenne muscular dystrophy (DMD) and myotonic dystrophy (DM). DM is another 'dynamic mutation' disease, similar to Huntington disease, that involves the expansion of a nucleotide repeat, this time in a muscle protein kinase gene. DMD involves a defect in the cytoskeletal protein, dystrophin, which is important for maintaining cell structure.

As used herein, "a nervous system disease or disorder" refers to a pathological condition caused by defects in the nervous system including the central nervous system, i.e., brain, and the peripheral nervous system. The brain and nervous system form an intricate network of electrical signals that are responsible for coordinating muscles, the senses, speech, memories, thought and emotion. Several diseases that directly affect the nervous system have a genetic component: some are due to a mutation in a single gene, others are proving to have a more complex mode of inheritance. As our understanding of the pathogenesis of neurodegenerative disorders deepens, common themes begin to emerge: Alzheimer brain plaques and the inclusion bodies found in Parkinson disease contain at least one common component, while Huntington disease, fragile X syndrome and spinocerebellar atrophy are all 'dynamic mutation' diseases in which there is an expansion of a DNA repeat sequence. Apoptosis is emerging as one of the molecular mechanisms invoked in several neurodegenerative diseases, as are other, specific, intracellular signaling events. The biosynthesis of myelin and the regulation of cholesterol traffic also figure in Charcot-Marie-Tooth and Neimann-Pick disease, respectively.

As used herein, "a signal disease or disorder" refers to a pathological condition caused by defects in the signal transduction process. Signal transduction within and between cells mean that they can communicate important information and act upon it. Hormones released from their site of synthesis carry a message to their target site, as in the case of leptin, which is released from adipose tissue (fat cells) and transported via the blood to the brain. Here, the leptin signals that enough has been eaten. Leptin binds to a receptor on the surface of hypothalamus cells, triggering subsequent intracellular signaling networks. Intracellular signaling defects account for several diseases, including cancers, ataxia telangiectasia and Cockayne syndrome. Faulty DNA repair mechanisms are also invoked in pathogenesis, since control of cell division, DNA synthesis and DNA repair all are inextricably linked. The end-result of many cell signals is to alter the expression of genes (transcription) by acting on DNA-binding proteins. Some diseases are the result of a lack of or a mutation in these proteins, which stop them from binding DNA in the normal way. Since signaling networks impinge on so many aspects of normal function, it is not surprising that so many diseases have at least some basis in a signaling defect.

As used herein, "a transporter disease or disorder" refers to a pathological condition caused by defects in a transporter, channel or pump. Transporters, channels or pumps that reside in cell membranes are key to maintaining the right balance of ions in cells, and are vital for transmitting signals from nerves to tissues. The consequences of defects in ion channels and transporters are diverse, depending on where they are located and what their cargo is. For example, in the heart, defects in potassium channels do not allow proper transmission of electrical impulses, resulting in the arrhythmia seen in long QT syndrome. In the lungs, failure of a sodium and chloride transporter found in epithelial cells leads to the congestion of cystic fibrosis, while one of the most common inherited forms of deafness, Pendred syndrome, looks to be associated with a defect in a sulphate transporter.

As used herein, "infection" refers to invasion of the body of a multi-cellular organism with organisms that have the potential to cause disease.

As used herein, "infectious organism" refers to an organism that is capable to cause infection of a multi-cellular organism. Most infectious organisms are microorganisms such as viruses, bacteria and fungi.

As used herein, "bacteria" refers to small prokaryotic organisms (linear dimensions of around 1 $\mu$m) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are 3 main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to obligate intracellular parasites of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungi" refers to a division of eucaryotic organisms that grow in irregular masses, without roots, stems, or leaves, and are devoid of chlorophyll or other pigments capable of photosynthesis. Each organism (thallus) is unicellular to filamentous, and possess branched somatic structures (hyphae) surrounded by cell walls containing glucan or chitin or both, and containing true nuclei.

B. Oligonucleotide Probe Containing a Hairpin Structure

In one aspect, the present invention provides an oligonucleotide probe for hybridization analysis, which probe comprises a nucleotide sequence which, under suitable conditions, is capable of forming a hairpin structure, wherein the double stranded segment of the hairpin structure is formed between two perfectly matched nucleotide sequences, and wherein at least a portion of the nucleotide sequence within the double stranded segment is complementary to a target nucleotide sequence to be detected.

The probe can comprise any kind of oligonucleotide or nucleic acid strand(s) containing genetically-coded and/or naturally occurring structures. The hairpin probes used herein can comprise DNA, RNA, or a combination of DNA and RNA. Hairpin probes also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides. For example, in one embodiment of the invention, hairpin probes comprising both DNA and RNA are designed such that DNA of the probe contains a sequence of nucleotides that are complementary to an RNA sequence of the probe running in opposite directions, such that upon intramolecular hybridization, the double stranded portion of the hairpin probe has DNA hybridized to RNA. Alternatively, or in addition, one or both of the complementary sequences of the intramolecularly hybridizing portion of the hairpin probe can be made resistant to a particular nuclease. For example, a methylphosphonate DNA sequence is resistant to cleavage by RNase H.

Within the probe, at least a portion of nucleotide sequence complementary to a target nucleotide sequence to be detected must be located within the double stranded segment. Preferably, the nucleotide sequence complementary to a target nucleotide sequence to be detected is completely located within the double stranded segment.

The probe can further comprise an element or a modification that facilitates intramolecular crosslinking of the probe upon suitable treatment. Such an element can be a chemically or photoactively activatable crosslinking agent, e.g., furocoumarins. Alternatively, such element can be a macromolecule having multiple ligand binding sites, e.g., component(s) of biotin-avidin binding system or an antigen-antibody binding system.

The probe can further comprise an element or a modification that renders the probe sensitive or resistant to nuclease digestion. For example, such an element can be a restriction enzyme cleavage site. In another example, at least a portion of the double stranded segment of the probe is a duplex between a DNA strand and a RNA strand, said DNA strand contains methylphosphonates and at least a portion of said RNA strand is complementary to a target nucleotide sequence to be detected. The methylphosphonate DNA:RNA hybrid in the probe itself is resistant to RNase H cleavage. However, once the probe hybridizes with a target DNA sequence, the RNA strand in the formed RNA:DNA duplex can be removed with RNase H treatment.

Probe sequences that are designed to hybridize intramolecularly or intermolecularly should be sufficiently complementary to hybridize under the selected conditions. Sufficient complementarity exists when an RNA or DNA strand will hybridize under selective hybridization conditions to its complement. Typically, selective hybridization will occur when there is at least about 65% complementarity over a stretch of at least 14 to 25 nucleotides, preferably at least about 75%, more preferably at least about 90% complementarity (See e.g., Kanehisa, *Nucleic Acids Res.,* 12:203 (1984)).

The intramolecular hybridization sequences in the hairpin probe can be separated by a flexible linker essentially as described in U.S. Pat. No. 5,556,752 to Lockhart et al. Briefly, the flexible linker is chosen to be of sufficient length and of sufficient materials to enable effective intramolecular probe hybridization. The length of the linker will typically be a length which is at least the length spanned by two nucleotide monomers and preferably at least four nucleotide monomers, while not being so long as to interfere with either the pairing of the complementary (anti-parallel) intramolecularly hybridizing probe sequences. The flexible linker can be DNA, RNA or any of a variety of chemical structures.

A hairpin probe can be prepared by synthesizing a single polynucleotide. Alternatively, one can separately synthesize each portion of the probe involved in intramolecular hybridization and then couple the portions together as a single hairpin probe by conjugation to each end of a separately prepared flexible linker. In this case, the flexible linker includes a linking group typically an alkylene group (of from about 6 to about 24 carbons in length), a polyethyleneglycol group (of from about 2 to about 24 ethyleneglycol monomers in a linear configuration), a polyalcohol group, a polyamine group (e.g., spermine, sperrnidine and polymeric derivatives thereof), a polyester group (e.g., poly(ethyl acrylate) having from about 3 to 15 ethyl acrylate monomers in a linear configuration), a polyphosphodiester group, or a polynucleotide (having from about 2 to about 12 nucleic acids). Preferably, the linking group will be a polyethyleneglycol group which is at least a tetraethyleneglycol, and more preferably, from about 1 to 4 hexaethyleneglycols linked in a linear array.

When synthesizing the hairpin probe from a separate flexible linker and separate intrahybridizing sequence portions of the hairpin probe, the flexible linker will be provided with functional groups at each end that can be suitably protected or activated. The functional groups are covalently attached to each portion of the probe via an ether, ester, carbamate, phosphate ester or amine linkage to either the 5'-hydroxyl or the 3'-hydroxyl of the probe portions chosen such that the complementary intramolecularly hybridizing sequences are in an anti-parallel configuration. Preferred linkages are phosphate ester linkages similar to typical oligonucleotide linkages. For example, hexaethyleneglycol can be protected on one terminus with a photolabile protecting group (i.e., NVOC or MeNPOC) and activated on the other terminus with 2-cyanoethyl-N,N-diisopropylamino-chlorophosphite to form a phosphoramidite. This linking group can then be used for construction of the probe libraries in the same manner as photolabile-protected, phosphoramidite-activated nucleotides. Other methods of forming ether, carbamate or amine linkages are known to those of skill in the art and particular reagents and references can be found in such texts as March, Advanced Organic Chemistry, 4th Ed., Wiley-Interscience, New York, N.Y., 1992.

Alternatively, naturally occurring oligonucleotides, or fragments thereof, may be isolated from their natural sources or purchased from commercial sources. Probe oligonucleotides can be generally be from nucleotides in length, preferably from about 6 to about 50 nucleotides, although oligonucleotides of different length may be appropriate. Suitable oligonucleotides may be prepared by the phosphoramidite method described by Beaucage and Carruthers, *Tetrahedron Lett.,* 22:1859–1862 (1981), or by the triester method according to Matteucci et al., *J. Am. Chem. Soc.,* 103:3185 (1981), or by other chemical methods using either a commercial automated oligonucleotide synthesizer or by VLSIPS™ technology (discussed in detail below).

C. Array of Oligonucleotide Probes Containing Hairpin Structures

In another aspect, the present invention provides an array of oligonucleotide probes immobilized on a solid support for hybridization analysis, which array comprises a solid support suitable for use in nucleic acid hybridization having immobilized thereon a plurality of oligonucleotide probes, each of the probes comprising a nucleotide sequence which, under suitable conditions, is capable of forming a hairpin structure and wherein at least a portion of the nucleotide sequence located within said double stranded segment is complementary to a target nucleotide sequence to be detected.

Within the probes, the double stranded segment of the hairpin structure can be formed between two perfectly matched nucleotide sequences. Alternatively, the double stranded segment of the hairpin structure can be formed between two imperfectly matched nucleotide sequences.

The plurality of probes can comprise DNAs, RNAs, derivatives thereof, or combinations thereof as described in the above Section B.

Within the probes, at least a portion of nucleotide sequence complementary to a target nucleotide sequence to be detected must be located within the double stranded segment. Preferably, the nucleotide sequence complementary to a target nucleotide sequence to be detected is completely located within the double stranded segment.

The probes can further comprise an element or modification that facilitates intramolecular crosslinking of the probes upon suitable treatment, and/or an element or modification that renders the probe sensitive or resistant to nuclease digestion, as described in the above Section B.

Immobilization of Hairpin Probes

Hairpin probes are preferably immobilized to a solid support such as biochip. The solid support may be biological, nonbiological, organic, inorganic, or a combination of any of these, existing as particles, strands, precipitates, gels, sheets, tubing, spheres, containers, capillaries, pads, slices, films, plates, slides, etc.

A solid support for immobilizing probes is preferably flat, but may take on alternative surface configurations. For example, the solid support may contain raised or depressed regions on which probe synthesis takes place or where probes are attached. In some embodiments, the solid support can be chosen to provide appropriate light-absorbing characteristics. For example, the support may be a polymerized Langmuir Blodgett film, glass or functionalized glass, Si, Ge, GaAs, GaP, $SiO_2$, $SiN_4$, modified silicon, or any one of a variety of gels or polymers such as (poly) tetrafluoroethylene, (poly)vinylidendifluoride, polystyrene, polycarbonate, or combinations thereof. Other suitable solid support materials will be readily apparent to those of skill in the art.

The surface of the solid support can contain reactive groups, which could be carboxyl, amino, hydroxyl, thiol, or the like suitable for conjugating to a reactive group associated with an oligonucleotide or a nucleic acid. Preferably, the surface is optically transparent and will have surface Si—OH functionalities, such as are found on silica surfaces.

Hairpin probes can be attached to the solid support by chemical or physical means such as through ionic, covalent or other forces well known in the art. Immobilization of nucleic acids and oligonucleotides can be achieved by means well known in the art (see, e.g., Dattagupta et al., *Analytical Biochemistry,* 177:85–89(1989); Saiki et al., *Proc. Natl. Acad. Sci. USA,* 86:6230–6234(1989); and Gravitt et al., *J. Clin. Micro.,* 36:3020–3027(1998)).

Hairpin probes can be attached to a solid support by means of a spacer molecule, e.g., essentially as described in U.S. Pat. No. 5,556,752 to Lockhart et al., to provide space between the double stranded portion of the probe as may be helpful in hybridization assays. A spacer molecule typically comprises between 6–50 atoms in length and includes a surface attaching portion that attaches to the solid support. Attachment to the support can be accomplished by carbon—carbon bonds using, for example, supports having (poly) trifluorochloroethylene surfaces, or preferably, by siloxane bonds (using, for example, glass or silicon oxide as the solid support). Siloxane bonding can be formed by reacting the support with trichlorosilyl or trialkoxysilyl groups of the spacer. Aminoalkylsilanes and hydroxyalkylsilanes, bis(2-hydroxyethyl)-aminopropyltriethoxysilane, 2-hydroxyethylaminopropyltriethoxysilane, arninopropyltriethoxysilane or hydroxypropyltriethoxysilane are useful are surface attaching groups.

The spacer can also include a extended portion or longer chain portion that is attached to the surface attaching portion of the probe. For example, amines, hydroxyl, thiol, and carboxyl groups are suitable for attaching the extended portion of the spacer to the surface attaching portion. The extended portion of the spacer can be any of a variety of molecules which are inert to any subsequent conditions for polymer synthesis. These longer chain portions will typically be aryl acetylene, ethylene glycol oligomers containing 2–14 monomer units, diamines, diacids, amino acids, peptides, or combinations thereof.

In some embodiments, the extended portion of the spacer is a polynucleotide or the entire spacer can be a polynucleotide. The extended portion of the spacer also can be constructed of polyethyleneglycols, polynucleotides, alkylene, polyalcohol, polyester, polyamine, polyphosphodiester and combinations thereof. Additionally, for use in synthesis of probes, the spacer can have a protecting group, attached to a functional group, e.g., hydroxyl, amino or carboxylic acid) on the distal or terminal end of the spacer (opposite the solid support). After deprotection and coupling, the distal end can be covalently bound to an oligomer or probe.

Microarray Formation

A variety of hairpin probes can be attached to a single solid support to form a microarray by procedures well known in the art . This is also referred to as a "micro array biochip" or "DNA biochip."

A microarry biochip containing a library of probes can be prepared by a number of well known approaches including, for example, light-directed methods, such as VLSIPS™, described in U.S. Pat. No. 5,143,854; mechanical methods such as described in PCT No. 92/10183 or U.S. Pat. No. 5,384,261; bead based methods such as described in U.S. Pat. No. 5,541,061; and pin based methods such as detailed in U.S. Pat. No. 5,288,514. U.S. Pat. No. 5,556,752 to Lockhart, which details the preparation of a library of different double stranded probes as a microarry using the VLSIPS™ also is suitable for preparing a library of hairpin probes in a microarray.

Flow channel methods, such as described in U.S. Pat. Nos. 5,677,195 and 5,384,261, can be used to prepare a microarry biochip having a variety of different hairpin probes. In this case, certain activated regions of the substrate are mechanically separated from other regions when the probes are delivered through a flow channel to the support. A detailed description of the flow channel method can be found in U.S. Pat. No. 5,556,752 to Lockhart et al., including the use of protective coating wetting facilitators to enhance the directed channeling of liquids though designated flow paths.

Spotting methods also can be used to prepare a microarry biochip with a variety of hairpin probes immobilized thereon. In this case, reactants are delivered by directly depositing relatively small quantities in selected regions of the support. In some steps, of course, the entire support surface can be sprayed or otherwise coated with a particular solution. In particular formats, a dispenser moves from region to region, depositing only as much probe or other reagent as necessary at each stop. Typical dispensers include a micropipette, nanopippette, ink-jet type cartridge or pin to deliver the probe containing solution or other fluid to the support and, optionally, a robotic system to control the position of these delivery devices with respect to the support. In other formats, the dispenser includes a series of tubes or multiple well trays, a manifold, and an array of delivery devices so that various reagents can be delivered to the reaction regions simultaneously. Spotting methods are well known in the art and include, for example those described in U.S. Pat. Nos. 5,288,514, 5,312,233 and 6,024,138. In some cases, a combination of flowing channel and "spotting" on predefined regions of the support also can be used to prepare microarry biochips with immobilized hairpin probes.

D. Methods for Detecting a Target Nucleotide Sequence in a Sample

In still another aspect, the present invention provides a method for detecting a target nucleotide sequence in a sample, comprising the steps of: a) providing an oligonucleotide probe comprising a nucleotide sequence having a hairpin structure, with a double stranded segment, wherein the double stranded segment is formed between two complementary, preferably two perfectly matched nucleotide sequences, and wherein at least a portion of the nucleotide sequence located within the double stranded segment is complementary to a target nucleotide sequence to be detected; b) contacting the probe provided in step a) with a sample containing or suspected of containing the target nucleotide sequence under conditions that favor intermolecular hybridization between the probe and the target nucleotide sequence over intramolecular hybridization of said probe itself; and c) assessing the intermolecular hybrid formed in step b) whereby presence of the intermolecular hybrid indicates the presence of the target nucleotide sequence in the sample.

Probes Used in the Method

To be used in the present methods, at least a portion of nucleotide sequence complementary to a target nucleotide sequence to be detected must be located within the double stranded segment. Preferably, the nucleotide sequence complementary to a target nucleotide sequence to be detected is completely located within the double stranded segment.

Hybridization Conditions

Any conditions that favor intermolecular hybridization between the probe and the target nucleotide sequence over intramolecular hybridization of the probe itself can be used in the present methods. Preferably, the conditions that favor intermolecular hybridization between the probe and the target nucleotide sequence over intramolecular hybridization of the probe itself is achieved by controlling compositions of the probe and the target nucleotide sequence so that the Tm of the intermolecular hybrid is higher than the Tm of the intramolecular hybrid. For example, when the intermolecular hybrid is a RNA:RNA hybrid, the intramolecular hybrid can be a RNA:DNA or a DNA:DNA hybrid. When the intermolecular hybrid is a RNA:DNA hybrid, the intramolecular hybrid can be a DNA:DNA hybrid. Normally, the Tm of the intermolecular hybrid is at least 2° C. higher than the Tm of the intramolecular hybrid. Preferably, the Tm of the intermolecular hybrid is at least 5° C. higher than the Tm of the intramolecular hybrid.

The hybridization between the hairpin probe and the target nucleotide sequence can be carried out under suitable stringencies, including high, middle or low stringency.

Detection of the Intermolecular Hybrid

Any suitable methods can be used in detecting the intermolecular hybrid formed between the probe and the target nucleotide sequence. For example, the direct labeling approach can be used, e.g., the target nucleotide sequence is detectably labeled and the formation of the intermolecular hybrid is assessed by detecting the label of the target nucleotide sequence in the intermolecular hybrid. Any suitable label can be used, including a chemical, an enzymatic, an radioactive, a fluorescent, a luminescent and a FRET (fluorescence resonance energy transfer) label.

The indirect labeling approach can also be used, i.e., the formation of the intermolecular hybrid is assessed by addition of a detectably labeled secondary probe that specifically hybridizes with at least a portion of the intermolecular hybrid and the detection of a secondary intermolecular hybrid formed between the secondary probe and the original intermolecular hybrid indicates the presence of said target nucleotide sequence in said sample.

When such indirect labeling approach is used, the method preferably further comprises a step of crosslinking the intermolecular hybrid and the intramolecular hybrid after the formation of the intermolecular hybrid but before the addition of the detectably labeled secondary probe. Any crosslinking method can used. For example, the crosslinking step can be effected via addition of a crosslinking agent subsequent to hybridization of the original probe with the target nucleotide sequence. Alternatively, the original hairpin probe can be synthesized with the crosslinking agent attached and crosslinking can be achieved by addition of an appropriate agent or treatment.

In one specific embodiment, the secondary probe specifically hybridizes with a portion of the target nucleotide sequence that is not involved in the hybridization of the target nucleotide sequence and the original probe.

In another specific embodiment, the secondary probe specifically hybridizes with a portion of the target nucleotide sequence that is involved in the hybridization of the target nucleotide sequence and the original probe and the nucleotide sequence in the original probe that is complementary to the same portion of the target nucleotide sequence is removed prior to or currently with the addition of the secondary probe. Many strategies can be used to ensure that the nucleotide sequence in the original probe that is complementary to the same portion of the target nucleotide sequence is removed prior to or currently with the addition of the secondary probe. For example, the hairpin structure in the original probe can be formed between a DNA strand that contains methylphosphonates and a RNA strand that is complementary to the target nucleotide sequence and wherein the RNA strand, after forming a hybrid with the target nucleotide sequence but before the addition of the secondary probe, is removed by a RNase H treatment.

In still another specific embodiment, the secondary probe specifically hybridizes with a portion of the original probe that is involved in the formation of the intramolecular hybrid but is not involved in the formation of the intermolecular hybrid with the target nucleotide sequence and wherein the same portion of the original probe that remains within the unhybridized original probe is removed prior to or currently with the addition of the secondary probe. Many strategies can be used to ensure that the same portion of the original probe that remains within the unhybridized original probe is removed prior to or currently with the addition of the secondary probe. For example, the portion of the original probe that remains within the unhybridized original probe contains a restriction enzyme cleavage site and is removed by cleavage with said restriction enzytne.

When detecting hybridization by an indirect detection method, a detectably labeled second probe(s) can be added after initial hybridization between the hairpin probe and the target or during hybridization of the hairpin probe and the target. When the labeled secondary probe is added after an initial hybridization reaction between the hairpin probe and the target, optionally, the immobilized hairpin probes can be subject to hybridization conditions that induce intramolecular hybridization of any non-intermolecularly hybridized hairpin probe. In this case, background hybridization between non-intermolecularly hybridized hairpin probe and a detectably labeled second probe is reduced upon subsequent hybridization.

After hybridization, unhybridized secondary probe can be separated from the hairpin probe by, for example, by washing if the hairpin probe is immobilized on a solid support. In the case of a solid support, detection of label bound to locations on the support indicates intermolecular hybridization of a target nucleotide sequence in the sample to the hairpin probe.

Secondary Probe

The detectably labeled secondary probe can be a specific probe. Alternatively, the detectably labeled probe can be a degenerate probe, e.g., a mixture of sequences such as whole genomic DNA essentially as described in U.S. Pat. No. 5,348,855. In the latter case, labeling can be conducted through use of intercalating dyes if the secondary probe contains double stranded DNA.

A secondary probe also can be a library of random nucleotide probe sequences. The length of a secondary probe should be decided in view of the length and composition of the primary probe or the target nucleotide sequence on the solid support that is to be detected by the secondary probe. Such a probe library is preferably provided with a 3' or 5' end labeled with photoactivatable reagent and the other end loaded with a detection reagent such as a fluorophore, enzyme, dye, luminophore, or other detectably known moiety.

The secondary probe can be detectably labeled by methods well known in the art including, for example, radioisotope, fluorophore, enzyme, dye, luminophore, or other detectably known moiety (See e.g., U.S. Pat. No. 5,348,855). For example, a variety of DNA-binding ligands are known to be useful for linking a nucleic acid secondary probe to a detectable the label. Particularly preferred DNA-binding ligands are intercalator compounds such as the fiurocoumarins, e.g., angelicin (isopsoralen) or psoralen or derivatives thereof, which photochemically react with nucleic acids, e.g., 4'-aminomethyl4,5'-dimethylangelicin, 4'-aminomethyl-trioxsalen (4'aminomethyl-4,5 ',8-trimethyl-psoralen), 3-carboxy-5-or-8-amino-or-hydroxy-psoralen, as well as mono-or bis-azido aminoalkyl methidium or ethidium compounds.

Particularly useful photoreactive forms of intercalating agents are the azidointercalators. Their reactive nitrenes are readily generated at long wavelength ultraviolet or visible light and the nitrenes of arylazides prefer insertion reactions over their rearrangement products (White et al., *Meth. Enzymol.*, 46:644 (1977)). Representative intercalating agents include azidoacridine, ethidium monoazide, ethidium diazide, ethidium dimer azide (Mitchell et al., *J. Am. Chem. Soc.*, 104:4265 (1982)), 4-azido-7-chloroquinoline, and 2-azidofluorene. A specific nucleic acid binding azido compound has been described by Forster, et al. *Nucleic Acid Res.*, 13:745 (1985). Other useful photoreactable intercalators are the furocoumarins which form (2+2) cycloadducts with pyrimidine residues. Alkylating agents also can be used as the DNA binding ligand, including, for example, bis-chloroethylamines and epoxides or aziridines, e.g., aflatoxins, polycyclic hydrocarbon epoxides, mitomycin and norphillin A.

Particularly useful labels are enzymatically active groups such as enzymes (Wisdom, *Clin. Chem.*, 22:1243 (1976)); enzyme substrates (British Pat No. 1,548,741); coenzymes (U.S. Pat. Nos. 4,230,797 and 4,238,565) and enzyme inhibitors (U.S. Pat. No. 4,134,792; fluorescers (Soini and Hemmila, *Clin. Chem.*, 25:353 (1979)); chromophores including phycobiliproteins, luminescers such as chemiluminescers and bioluminescers (Gorus and Schram, *Clin. Chem.*, 25:512 (1979) and ibid, 1531); specifically bindable ligands, i.e., protein binding ligands; antigens; and residues comprising radioisotopes such as $^3H$, $^{35}S$, $^{32}P$, $^{125}I$, and $^{14}C$. Such labels are detected on the basis of their own physical properties (e.g.; fluorescers, chromophores and radioisotopes) or their reactive or binding properties (e.g., enzymes, substrates, coenzymes and inhibitors).

For example, a cofactor-labeled nucleic acid can be detected by adding the enzyme for which the label is a cofactor and a substrate for the enzyme. A hapten or ligand (e.g., biotin) labeled nucleic acid can be detected by adding an antibody or an antibody pigment to the hapten or a protein that binds the ligand (e.g., avidin), tagged with a detectable molecule. A detectable molecule has a measurable physical property (e.g., fluorescence or absorbance) or is participant in an enzyme reaction (e.g., see above list). For example, one can use an enzyme which acts upon a substrate to generate a product with a measurable physical property. Examples of the latter include, but are not limited to, beta-galactosidase, alkaline phosphatase, papain and peroxidase. For in situ hybridization studies, the final product of the substrate is preferably water insoluble. Other labels, e.g., dyes, will be evident to one having ordinary skill in the art.

If the label is an enzyme, the labeled DNA is ultimately placed in a suitable medium to determine the extent of catalysis. Thus, if the enzyme is a phosphatase, the medium can contain nitrophenyl phosphate and one can monitor the amount of nitrophenol generated by observing the color. If the enzyme is a beta-galactosidase, the medium can contain o-nitro-phenyl-D-galacto-pyranoside, which also liberates nitrophenol. The label can be linked to the DNA binding ligand, e.g., acridine dyes, phenanthridines, phenazines, furocoumarins, phenothiazines and quinolines, by direct chemical linkage such as involving covalent bonds, or by indirect linkage such as by the incorporation of the label in a microcapsule or liposome, which in turn is linked to the binding ligand. Methods by which the label is linked to a DNA binding ligand such as an intercalator compound are well known in the art and any convenient method can be used.

Advantageously, the DNA binding ligand is first combined with label chemically and thereafter combined with the nucleic acid secondary probe. For example, since biotin carries a carboxyl group, it can be combined with a furocoumarin by way of amide or ester formation without interfering with the photochemical reactivity of the furocoumarin or the biological activity of the biotin. Aminomethylangelicin, psoralen and phenanthridium derivatives can similarly be linked to a label, as can phenanthridium halides and derivatives thereof such as aminopropyl methidium chloride (Hertzberg et al, *J. Amer. Chem. Soc.*, 104:313 (1982)). Alternatively, a bifunctional reagent such as dithiobis succinimidyl propionate or 1,4-butanediol diglycidyl ether can be used directly to couple the DNA binding ligand to the label where the reactants have alkyl amino residues, again in a known manner with regard to solvents, proportions and reaction conditions. Certain bifunctional reagents, possibly glutaraldehyde may not be suitable because, while they couple, they may modify nucleic acid and thus interfere with the assay. Routine precautions can be taken to prevent such difficulties.

The particular sequence used in making the labeled nucleic acid can be varied. Thus, for example, an amino-substituted psoralen can first be photochemically coupled with a nucleic acid, the product having pendant amino groups by which it can be coupled to the label, i.e., labeling is carried out by photochemically reacting a DNA binding ligand with the nucleic acid in the test sample. Alternatively, the psoralen can first be coupled to a label such as an enzyme and then to the nucleic acid.

Also advantageously, the DNA binding ligand can be linked to the label by a spacer, which includes a chain of up to about 40 atoms, preferably about 2 to 20 atoms, selected from the group consisting of carbon, oxygen, nitrogen and sulfur. Such spacer can be the polyfunctional radical of a member selected from the group consisting of peptide, hydrocarbon, polyalcohol, polyether, polyarnine, polyimine and carbohydrate, e.g., -glycyl-glycyl-glycyl- or other oligopeptide, carbonyl dipeptides, and omega-amino-alkane-carbonyl radical or the like. Sugar, polyethylene oxide radicals, glyceryl, pentaerythritol, and like radicals also can serve as spacers. Spacers can be directly linked to the nucleic acid-binding ligand and/or the label, or the linkages may include a divalent radical of a coupler such as dithiobis succinimidyl propionate, 1,4-butanediol diglycidyl ether, a diisocyanate, carbodiimide, glyoxal, glutaraldehyde, or the like.

The detectable label can be visualized or assessed by placing the probe array next to x-ray film or phosphorimagers to identify the sites where the secondary probe has bound. Fluorescence can be detected by way of a charge-coupled device (CCD) or laser scanning.

The detectably labeled secondary probe(s) can be added after hybridization or during hybridization of the test sample to the hairpin probe. Optionally the hybridization conditions may be modified after addition of the secondary probe. After hybridization, unhybridized secondary probe is separated from the hairpin probe by, for example, washing if the hairpin probe is immobilized on a solid support. In the case of a solid support, detection of label bound to locations on the support indicates intermolecular hybridization of a target nucleotide sequence in the sample to the hairpin probe.

A secondary probe for indirect detection of hybridization can be detected by energy transfer such as in the "beacon probe" method described by Tyagi and Kramer, *Nature Biotech.*, 14:303–309 (1996) or U.S. Pat. Nos. 5,119,801 and 5,312,728 to Lizardi et al. The secondary probes used herein can be a hairpin probe with a donor fluorophore at one end of the probe and an acceptor moiety, usually a quencher, at the other end of the probe. Thus when the secondary probe is in the open conformation, the fluorescence of the donor fluorophore is detectable, whereas when the second probe is in a hairpin or closed conformation, the fluorescence of the donor fluorophore is quenched. Any FRET detection system known in the art can be used in the present method. For example, the AlphaScreen™ system can be used. AlphaScreen technology is an "Amplified Luminescent Proximity Homogeneous Assay" method. Upon illumination with laser light at 680 nm, a photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity of the donor bead, by virtue of a biological interaction, the singlet-state oxygen molecules reacts with chemiluminescent groups in the acceptor beads, which immediately transfer energy to fluorescent acceptors in the same bead. These fluorescent acceptors shift the emission wavelength to 520–620 nm. The whole reaction has a 0.3 second half-life of decay, so measurement can take place in time-resolved mode. Other exemplary FRET donor/acceptor pairs include Fluorescein (donor) and tetramethyl-rhodamine (acceptor) with an effective distance of 55 Å; IAEDANS (donor) and Fluorescein (acceptor) with an effective distance of 46 Å; and Fluorescein (donor) and QSY-7 dye (acceptor) with an effective distance of 61 Å (Molecular Probes).

Quantitative assays for nucleic acid detection also can be performed according to the present invention. The amount of secondary probe bound to a microarry spot can be measured and can be related to the amount of nucleic acid target which is in the sample. Dilutions of the sample can be used along with controls containing known amount of the target nucleic acid. The precise conditions for performing these steps will be apparent to one skilled in the art.

Embodiments to Reduce Secondary Probe Background Binding

The present invention provides several embodiments useful for reducing background hybridization under indirect detection occurring when the secondary probe hybridizes to unhybridized (i.e., non-intermolecularly hybridized) hairpin probe on the solid support.

1. Hairpin Formation of Unhybridized Hairpin Probes:

Subsequent to achieving intermolecular probe hybridization to target nucleic acid, conditions are adjusted to support intramolecular hybridization for all unhybridized hairpin probes. Detectably labeled secondary probe is then added and the binding subsequently determined.

2. Crosslinking of Unhybridized Hairpin Probes:

Cross linking can be achieved by covalent or noncovalent strategies. Covalent intermolecular crosslinking of intramolecular hybridized probe is achieved by an agent such as psoralen. Such agent can be incorporated into the secondary probe during its preparation or can be added to the probe-target hybridization mixture following the step of intermolecular hybridization.

Noncovalent crosslinking of intramolecular hybridized probe is achieved by a ligand-receptor interaction such as avidin-biotin. For example, the probe can be synthesized with at least two biotin moieties, one in each arm of the hybridizing hairpin suitable for crosslinking by avidin or streptavidin.

In either approach, probe crosslinking is optionally preceded with the use of a hybridization step that supports intramolecular hairpin formation.

3. Differential Destruction of Inter-Versus Intra-Molecularly Hybridized Probe

In this embodiment, the hairpin probe is prepared comprising a modified phosphodiester nucleotide DNA sequence in one strand of the double stranded portion of the probe and a complementary RNA sequence or DNA sequence in the other strand of the double stranded portion of the probe, wherein the modified phosphodiester nucleotide DNA is not recognizable by a particular DNA or RNA nuclease. Following hybridization of the target sample nucleic acid or optionally following a subsequent step of providing hybridization conditions supporting intramolecular hybridization of unhybridized probe, the nuclease is added to partially degrade the intermolecularly hybridized probe, thereby exposing an unique DNA sequence not available in the intramolecularly hybridized probe. A detectably labeled secondary probe that hybridizes with the unique exposed sequence is then used to detect original intermolecular hybridization between the target and the hairpin probe (which occurred prior to nuclease digestion of this hybrid).

For example, the hairpin probe can be prepared with methylphosphonate DNA for one intramolecularly hybridizing sequence and with RNA for the other intramolecularly hybridizing sequence. When such a probe is intermolecularly hybridized to a target nucleic acid, the RNA portion of the hairpin is sensitive to digestion with RNase H, which destroys the hybrid but which results in a single stranded methylphosphonate DNA sequence that is now available for detection by hybridization to an appropriate complementary secondary probe. The background is reduced in this format because probes that do not intermolecularly hybridize are not subject to degradation by the nuclease and do not have the unique exposed sequence to hybridize with the secondary probe.

In another example, certain enzymatic digestions, e.g., restriction enzyme digestion, can be used to selectively protect intermolecularly hybridized probe and target nucleotide sequence. After hybridization, such enzymatic cleavage sites can be created in either the probe or the intermolecular hybrid. For example, certain restriction enzymes, e.g., BstNI, do not cleave single-stranded substrate. After hybridization with the target DNA, a portion of the hybridized DNA becomes single-stranded and is resistant to the BstNI digestion, whereas the unhybridized DNA probe remains double-stranded and is sensitive to the BstNI digestion. Other variations can be made so that the hybridized probe, but not the unhybridized probe, is sensitive to the enzymatic digestion. This can be achieved by using modified nucleotides in the intramolecular probe hybrids which renders it resistant to the enzymatic digestion. After intermolecular hybridization, enzymatic cleavage sites can be created in the intermolecular hybrid (see e.g., U.S. Pat. No. 5,932,450). Such modifications include the use of methylphosphonates, phosphorothioates, peptide internucleotides and other suitable moieties and/or linkages in the hairpin probe.

Test Samples and Target Nucleotide Sequences

Target nucleotide sequences detectable using the hybridization methods disclosed herein can be DNA, RNA or any other naturally or synthetic nucleic acid sample. Test samples can include body fluids, such as urine, blood, semen, cerebrospinal fluid, pus, amniotic fluid, tears, or semisolid or fluid discharge, e.g., sputum, saliva, lung aspirate, vaginal or urethral discharge, stool or solid tissue samples, such as a biopsy or chorionic villi specimens. Test samples also include samples collected with swabs from the skin, genitalia, or throat. Test samples can be processed to isolate nucleic acid by a variety of means well known in the art.

Although the present method can be used in solution, it is preferably conducted in chip format, e.g., by using the probe(s) immobilized on a solid support.

Similarly, although the present method can be used to analyze a single sample with a single probe at a time. Preferably, the method is conducted in high-throughput format. For example, a plurality of samples can be analyzed with a single probe simultaneously, or a single sample can be analyzed using a plurality of probes simultaneously. More preferably, a plurality of samples can be analyzed using a plurality of probes simultaneously.

Any suitable samples can be analyzed using the present method. Preferably, a biosample is analyzed using the present method. For example, a biosample of plant, animal, human, fungus, bacterium and virus origin can analyzed. If a sample of a mammal or human origin is analyzed, the sample can be derived from a particular tissue or organ. Exemplary tissues include connective, epithelium, muscle or nerve tissue. Exemplary organs include eye, annulospiral organ, auditory organ, Chievitz organ, circumventricular organ, Corti organ, critical organ, enamel organ, end organ, external female gential organ, external male genital organ, floating organ, flower-spray organ of Ruffi, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subfornical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl. Preferably, samples derived from an internal mammalian organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc, are analyzed.

Alternatively, pathological samples in connection with various diseases or disorders or infections can be analyzed. Exemplary diseases or disorders include neoplasms (neoplasia), cancers, immune system diseases or disorders, metabolism diseases or disorder, muscle and bone diseases or disorders, nervous system diseases or disorders, signal diseases or disorders and transporter diseases or disorders. The infection to be analyzed can be fungal, bacterial and viral infection.

The present methods can be used to detect or analyze any nucleic acids from essentially any species of organism, including, for example, Acintobacter, Actinomyces, Aerococcus, Aeromonas, Alclaigenes, Bacillus, Bacteriodes, Bordetella, Branhamella, Bevibacterium, Campylobacter, Candida, Capnocytophagia, Chlamydia, Chromobacterium, Clostridium, Corynebacterium, Cryptococcus, Deinococcus, Enterococcus, Erysielothrix, Escherichia, Flavobacterium, Gemella, Gonorrhea, Haemophilus, Kilebsiella, Lactobacillus, Lactococcus, Legionella, Leuconostoc, Listeria, Micrococcus, Mycobacterium, Neisseria, Nocardia, Oerskovia, Paracoccus, Pediococcus, Peptostreptococcus, Propionibacterium, Proteus, Psuedomonas, Rahnella, Rhodococcus, Rhodospirillium, Staphlococcus, Streptomyces, Streptococcus, Vibrio, and Yersinia. Also included are viruses such as the hepatitis viruses and human immunodeficiency viruses (HIV).

E. Method for Detecting a Target Nucleotide Sequence Using Immobilized Probe Arrays In yet another aspect, the present invention provides a method for detecting a target nucleotide sequence in a sample, comprising the steps of: a) providing an array of oligonucleotide probes immobilized on a solid support suitable for use in nucleic acid hybridization having immobilized thereon a plurality of oligonucleotide probes, each of the probes comprising a hairpin structure with a double stranded segment and wherein at least a portion of the nucleotide sequence located within the double stranded segment is complementary to a target nucleotide sequence to be detected; b) contacting the array of probes provided in step a) with a sample containing or suspected of containing the target nucleotide sequence under conditions that favor intermolecular hybridization between the probes and the target nucleotide sequence over intramolecular hybridization of the probes themselves; and c) assessing the intermolecular hybrids formed in step b), whereby presence of the intermolecular hybrids indicates the presence of the target nucleotide sequence in the sample.

Within the probes used in the array, the double stranded segment of the hairpin structure can be formed between two perfectly matched nucleotide sequences. Alternatively, within the probes used in the array, the double stranded segment of the hairpin structure can be formed between two imperfectly matched nucleotide sequences.

Hybridization conditions, means for detecting the intermolecular hybrid, the secondary probes and test samples and target nucleotide sequences described in the above Section E can also be used in connection with the method described in this Section F.

F. EXAMPLES

Example 1
Human Papilloma Virus Genotyping

Immobilization of nucleic acids and oligonucleotides are known in the art (Dattagupta et al., *Analytical Biochemistry*, 177:85–89 (1989); Saiki et al., *Proc. Natl. Acad Sci., USA*, 86:6230–6234 (1989); and Gravitt et al., *J. Clin. Micro.*, 36:3020–3027 (1998)). Methods described in those references can be used in the present invention human papilloma virus (HPV) probe sequences as described in Gravitt et al., (supra) are synthesized in a commercially available oligonucleotide synthesizer. During the synthesis, following changes are made:
  i) The probes are extended at the 3' end up to 30 extra nucleotide residues. First 9 residues are made of dT to function as spacer for the hairpin structure.
  ii) The rest (21 residues) is complementary to the probe sequence and sequentially organized as 7 deoxy-6 ribo-8 deoxy residues.
  iii) The probe sequence has methylphosphonates complementary to the ribose residues in the chain. This will prevent RNase H digestion of the unhybridized hairpin probe. This will also reduce the Tm of the probe compared to an RNA-DNA hybrid formed with a target.

For example, the probe 5'-CAT CCG TAA CTA CAT CTT CCA-3' (SEQ ID NO: 1) is present in an oligonucleotide of the following structure:
  5'-CAT-CCG-TAa-cta-caT-CTT-CCA-TTT-TTT-TTT-TGG-AAG A UG-UAG-UTA-CGG-ATG-3' (SEQ ID NO:2) (underlined nucleotides are ribonucleotides, lower case nucleotides are methylphosphonates residues). Such an oligonucleotide is immobilized onto a membrane by BSA conjugation method and genomic HPV DNA is purified from samples by proteinase K digestion and ethanol precipitation as described in Gravitt et al (supra). The immobilized hairpin probe containing strip is hybridized with the sample DNA at 53° C. overnight in a buffer containing 0.72 M NaCl, 40 mM $NaH_2PO_4$ and 4 mM EDTA (pH 7.7). After hybridization, the strip is washed twice with the hybridization buffer at 57° C. and RNase H buffer once. The strip containing the hybrid is then treated with RNase H to digest the part of the hybridized probe with RNA-DNA hybrid structure. This is carried out by using 1 unit of RNase H from Sigma Chemical Co. (St. Louis, Mo.) per ml of the digestion buffer. The RNase H digestion buffer contains 20 mM tris-HCl (pH 7.5), 100 mM KCl, 10 mM $MgCl_2$, 0.1 mM EDTA, 0.1 mM DTT and 0.05 mg BSA per ml. By immersing the strip containing the hybrid in the digestion buffer containing the enzyme for 1 hour at 37° C., hybrids containing RNA-DNA structure is digested and under these conditions hairpin intra-molecular hybrid is not disturbed.

After the enzyme digestion, the strip is washed with hybridization buffer and a second hybridization is carried out with biotin labeled probes. The labeled probes are equal weight by weight mixtures of oligonucleotides complementary to the immobilized probe portions which become single stranded after hybridization and digestion. After the second hybridization and washing, biotin in the hybrid is detected by using a streptavidin-horseradish peroxidase conjugate chemiluminescence. This is carried out by soaking the array in a solution containing 1:1 mixture of 0.5 mM Luminol and hydrogen peroxide and wrapping the whole contents with a plastic wrap, e.g., "SARAN WRAP". The light emission is recorded on a "POLAROID" film. Biotin sites appear as white spots on the film.

The sites where biotin is detected is the site of hybridization of the target sample and the corresponding sequence is the sequence of the target present in the sample.

Example 2
Assay for Mycobacterium TB Drug Resistance by Post Hybridization Blocking of Immobilized Probes Using the sequence information disclosed in Telenti et al., *Lancet*, 341:647–650 (1993), Beenhouwer et al., *Tubercule and Lung Disease*, 76:425–430 (1995) designed PCR primers and probes for detection of mutated sequence in a rifampicin resistance of mycobacterium tuberculosis organism. The present method uses identical primers for PCR and immobilized probe sequences. The probe sequences are extended as described in example 1 to have a hairpin structure which is immobilized and at nucleotide position 45 a psoralen moiety is covalently attached.

Primer sequences for amplification are:
  5'GAG AAT TCG GTC GGC GAG CTG ATCC 3' (SEQ ID NO:3) and
  5'CGA AGC TTG ACC CGC GCG TAC ACC 3' (SEQ ID NO:4).

These primers produce a 395 bp amplicon after PCR. PCR is done in a buffer containing 50 mM KCl, 10 mM tris-HCl (pH 8.3), 2.2 mM MgCl$_2$, 200 mM each of four dNTPs, 0.01% gelatin and 1U of Taq Polymerase. Typical amplification is done for 40 cycles (94° C., 58° C. and 72° C. at 45 sec.) For the synthesis of labeled amplicons as detection probe, PCR is done by using a mixture of dNTPs containing biotinylated dUTP and TTP in a 1:10 mixture and others in the same concentrations as above.

A typical 48-mer long hairpin probe has the following structure after immobilization:

5'**CAA TTC ATG GAC CAG AAC AAC CCG TTT TTT TTT CGG GTT GTT CTG CTC CAT GAA TTG 3' (SEQ ID NO:5). The sequence underlined is synthesized in an oligonucleotide synthesizer. In between nucleotides TT a psoralen modification is used to crosslink unhybridized hairpin probe after hybridization with the sample. First, the oligonucleotide with an amino terminated linker in the TT position is synthesized in a synthesizer. Such linkers have been described in U.S. Pat. No. 5,541,313. The amino terminated linker containing oligonucleotide is then reacted with an N-hydroxysuccinimide (NHS) activated 4'-carboxtrioxsalen derivative in dimethyl sulfoxide. Such a compound is synthesized by reacting 4'-arninomethyl trioxsalen (Sigma Chemical Co. St. Louis, Mo.) with succinic anhybride. The resulting carboxy compound is then further activated to produce NHS-ester which is used for the reaction. After the reaction the oligonucleotide is purified on a reverse phase HPLC column. The oligonucleotide is then phosphorylated at the 5'-end by conventional method using polynucleotide kinase. The solid support containing immobilized oligonucleotide of structure 5'-TTT TTT TTT CAA TTC ATG-3' (SEQ ID NO:6) is hybridized with 5'-phosphorylated GAC CAG AAC AAC CCG TTT TTT TTT CGG GTT GTT CTG CTC CAT GAA TTG-3' (SEQ ID NO:7). The hybrid is ligated by using a T4 DNA ligase. This produces an immobilized probe with a photocrosslinking moiety.

A set of immobilized probes on polystyrene beads with sequences of all different modifications representative of the mutations responsible for rifampicin resistance is prepared as describe above. Each immobilized probe is dispensed in a microtitre plate well. Five microliters of the amplicons are aliquoted into each well followed by 40 microliters of hybridization buffer of example 1. Hybridization is done at 56° C. for 60 minutes. After hybridization the beads are washed as described in example 1. The microtiter plate is exposed to 312 nm light for 60 minutes using a transilluminator at 25° C. This process crosslinks all unhybridized immobilized probes and hybrid(s) to the solid support. The hybrids are detected by a second hybridization with a labeled probe as the PCR amplicon containing biotin as described above. Biotin in the hybrid is detected by a streptavidin-horseradish peroxidase enzyme system.

Example 3

Post Hybridization Labeling of Hybrids

Example 2 is repeated without the use of biotinylated labeled amplicon. After hybridization, washing and irradiation, the hybrids are labeled for detection by hybridization with a aminomethyl trioxsalen and enzyme labeled degenerate pentamer oligonucleotides. The double labeled oligonucleotides are synthesized as follows:

First, a psoralen labeled ribonucleotide is synthesized as described in Dattagupta et al., U.S. Pat. No. 5,587,472. Commercially available aminomethyltrioxsalen from Sigma Chemical Co. is derivatized with a dibasic acid anhydride like succinic anhydride. The resulting acid is mixed with (1:3:3 molar ratio) 1-(3-dimethylaminopropyl)-3-ethylcarbodimide methiodide and N-hydroxysulfosuccinimide (sodium salt) in DMF and heated to 50° C. for 7.5 hours. According to TLC (toluene/ethanol 0.5:4, silicagel), most of the carboxylic acid has been converted to the N-hydroxysulfosuccininimide ester. The reaction mixture is cooled to room temperature and a solution of 8-(6-aminohexyl) mninoadenosine-5'-triphosphate (Li-salt, Sigma, $10^{-5}$ mol) in 100 $\mu$l water and 20 $\mu$l pyridine ($2.5 \times 10^{-4}$ mol) is added. After stirring at room temperature overnight, only traces of a new compound are detectable. The mixture is then sonicated for 3 hours, 2 mg of 4-dimethylaminopyridine ($1.6 \times 10^{-5}$) is added and the mixture is sonicated for an additional 5 hours. According to TLC (t-BuOH 3.5/acetone 2.5/conc. ammonia 1.5/HOAc 1.5/water, cellulose), a new product is now easily detectable. The reaction mixture is evaporated to dryness under vacuum. Chromatography of the residue (3 times) on a Sephadex G 10 column (Pharmacia) with water as eluent gives arninomethyltrioxsalen labeled ATP (ps-ATP).

The psoralen labeled ribonucleotide (ps-ATP described above) is incorporated into degenerate tetramer oligonucleotides by terminal deoxynucleotidyl transferase (Pharmacia) as follows:

1.8 $\mu$g oligonucleotide (synthesized in an Applied Biosystems Inc.'s (Foster City, Calif.) automated oligonucleotide synthesizer using their reagents) and 2.5 $\mu$g ps-ATP are dissolved in a reaction buffer containing 140 mmol/l K-cacodylate, 30 mmol/l Tris-buffer (pH 7.6), 1 mmol/l cobalt chloride and 0.1 mmol/l dithiothreitol (DTT) (total volume 50 $\mu$l). Enzymatic elongation is achieved by addition of 22 U terminal deoxynucleotidyl transferase and incubation for 16.5 hours at 37° C.

20% denaturing polyacrylamide gel electrophoresis shows a DNA band under UV shadowing which can be detected visually.

ps-ATP labeled oligonucleotide is further treated if necessary, with sodium hydroxide to digest all but the last ribonucleotide residue which contains one aminomethyl trioxsalen moiety.

Similar method can be used to synthesize oligonucleotide with any ribonucleotide (A,U,G, C ribo T or any other ribonucleoside or deoxyribonucleoside) at its 3' end.

All different degenerate sequences are made in a synthesizer. At the 3'-end of the pentamer, a psoralen moiety as described above and at the 5'-end an enzyme like horseradish peroxidase is covalently attached following the method described in U.S. Pat. No. 5,541,313. Such synthetic molecules are available commercially from Gemini Biotech Ltd. The Woodlands, Texas. These degenerate sequences hybridize to any complementary hybridizable sequence at 30° C. After hybridization and a second irradiation, the labeled petamers are covalently linked to the hybrid or single stranded hybridized probes. Unreacted pentamers are washed at 37° C. and hybrids are detected by the enzyme assay as described above.

The above examples are included for illustrative purposes only and is not intended to limit the scope of the invention. Since modifications will be apparent to those of skill in this art, it is intended that this invention be limited only by the scope of the appended claims.

What is claimed is:

1. A method for detecting a target nucleotide sequence in a sample comprising the steps of:
   a) providing an oligonucleotide probe comprising a nucleotide sequence that forms a hairpin structure having a stem region comprising a double stranded segment under suitable conditions, wherein the double stranded segment is formed between two complementary nucleotide sequences, and wherein at least a portion of at least one of the nucleotide sequences located within the double stranded segment is complementary to the target nucleotide sequence to be detected;
   b) contacting the probe provided in step a) with a sample containing or suspected of containing the target nucleotide sequence under conditions that favor intermolecular hybridization between the probe and the target nucleotide sequence over intramolecular hybridization of the probe itself, whereby the contacting breaks the intramolecular hybridization of the probe itself by dissociating the double stranded segment of the probe and forms a first intermolecular hybrid between the target and a region consisting of at least a portion of one strand of said stem that is complementary to the target nucleotide sequence; and
   c) assessing the first intermolecular hybrid formed in step b), wherein the assessing is effected by addition of a secondary probe that specifically hybridizes with at least a portion of the first intermolecular hybrid, thereby forming a secondary intermolecular hybrid formed between the secondary probe and the first intermolecular hybrid wherein the detection of the secondary intermolecular hybrid indicates the presence and/or amount of the target nucleotide sequence in the sample.

2. The method of claim 1, wherein the nucleotide sequence complementary to the target nucleotide sequence to be detected is completely located within the double stranded segment.

3. The method of claim 1, wherein the conditions that favor intermolecular hybridization between the probe and the target nucleotide sequence over intramolecular hybridization of the probe itself is achieved by controlling compositions of the probe and the target nucleotide sequence so that the Tm of the intermolecular hybrid is higher than the Tm of the intramolecular hybrid.

4. The method of claim 3, wherein the Tm of the intermolecular hybrid is at least 2° C. higher than the Tm of the intramolecular hybrid.

5. The method of claim 3, wherein the intermolecular hybrid is a RNA:RNA hybrid whereas the intramolecular hybrid is a RNA:DNA.

6. The method of claim 3, wherein the intermolecular hybrid is a RNA:DNA hybrid whereas the intramolecular hybrid is a DNA:DNA hybrid.

7. The method of claim 1, further comprising a step of crosslinking the stem region of the probe that has not been hybridized with the target after the formation of the first intermolecular hybrid but before the addition of the secondary probe.

8. The method of claim 7, wherein the crosslinking step is effected via addition of a crosslinking agent subsequent to hybridization of the probe with the target nucleotide sequence.

9. The method of claim 1, wherein the hairpin probe further comprises an element or a modification that facilitates intramolecular crosslinking of the probe upon a suitable treatment.

10. The meted of claim 9, wherein the element is a crosslinking agent that is activated by chemical or photoactive txeatment.

11. The method of claim 1, wherein the secondary probe specifically hybridizes with a portion of the target nucleotide sequence that is not involved in the hybridization of the target nucleotide sequence and the probe.

12. The method of claim 1, wherein the secondary probe specifically hybridizes with a portion of the target nucleotide sequence that is involved in the hybridization of the target nucleotide sequence and the probe and the nucleotide sequence in the probe that is complementary to the same portion of the target nucleotide sequence is removed concurrently with the addition of the secondary probe.

13. The method of claim 11, wherein the hairpin structure in the probe is formed between a DNA strand that contains methylphosphonates and a RNA strand that is complementary to the target nucleotide sequence and wherein the RNA strand, after forming a hybrid with the target nucleotide sequence but before the addition of the secondary probe, is removed by a RNase H treatment.

14. The method of claim 1, wherein the secondary probe specifically hybridizes with a portion of the probe that is involved in the formation of the intramolecular hybrid but is not involved in the formation of the first intermolecular hybrid with the target nucleotide sequence and wherein the portion of the probe dissociates as a single strand.

15. The method of claim 1, wherein the secondary probe is a specific probe.

16. The method of claim 1, wherein the secondary probe is a degenerate probe.

17. The method of claim 1, wherein the probe is immobilized on a solid support.

18. The method of claim 1, wherein the sample is a biosample.

19. The method of claim 1, wherein a plurality of samples is assayed simultaneously.

20. The method of claim 1, wherein the secondary probe has a detectable label.

21. The method of claim 20, wherein the label is selected from the group consisting of a chemical, an enzymatic, a radioactive, a fluorescent, a luminescent and a FRET label.

22. The method of claim 20, wherein the detectably labeled secondary probe is crosslinked to the first intermolecular hybrid before the secondary intermolecular hybrid is formed between the secondary probe and the first intermolecular hybrid.

23. The method of claim 1, wherein the probe further comprises an element that is sensitive to nuclease digestion or a modification that is resistant to nuclease digestion.

24. The method of claim 23, wherein the nuclease digestion is effected via a restriction enzyme or a RNase H.

* * * * *